Aug 21, 1951 F. A. NEWBERRY Plant Pat. 1,031

BERRY PLANT

Filed Aug. 8, 1947 3 Sheets-Sheet 1

INVENTOR
Frank A. Newberry
BY
Arnold and Mathis
ATTORNEYS

INVENTOR
Frank A. Newberry
BY
Arnold and Mathis
ATTORNEYS

INVENTOR
Frank A. Newberry
BY Arnold and Mathis
ATTORNEYS

Patented Aug. 21, 1951

Plant Pat. 1,031

UNITED STATES PATENT OFFICE 1,031

BERRY PLANT

Frank A. Newberry, Port Angeles, Wash.

Application August 8, 1947, Serial No. 767,637

1 Claim. (Cl. 47—62)

My invention relates to a new and distinct variety of berry plant.

The fruit of this new variety is large and delicately flavored partaking of some of the aspects of a raspberry and some of the aspects of a loganberry.

The annexed drawings and specifications to follow present the distinctions in characteristics of the variety of plant which has been asexually reproduced.

The plant of my invention was obtained by bringing loganberries, Cuthbert Raspberries and everbearing raspberries in close proximity to each other. The following year a sport appeared at the base of one of the loganberry plants. Careful and practical nursery attention was given to this sport to cause it to mature. Then other plants were produced from this sport and experimental plants were propagated to determine whether or not the plant could be caused to repropagate itself in kind and nature. The origin is further discussed hereinafter.

The plants of my invention are deep rooted, sturdy, and have been asexually reproduced in the State of Washington, near Port Angeles, Washington, and in the manner common to asexually reproducing varieties of raspberry plants. In other words, cuttings were taken from the stem of the sport previously mentioned, the cuttings were caused to root, and the rooted cuttings were replanted; and some of the plants so produced had their roots divided and separate plants were set out from the stems bearing such divided roots. When they are just starting (having a height of three to sixteen inches), they appear almost identical with young loganberries, and a great number of wine colored stickers are present. At maturity they are practically thornless.

Figure 1:
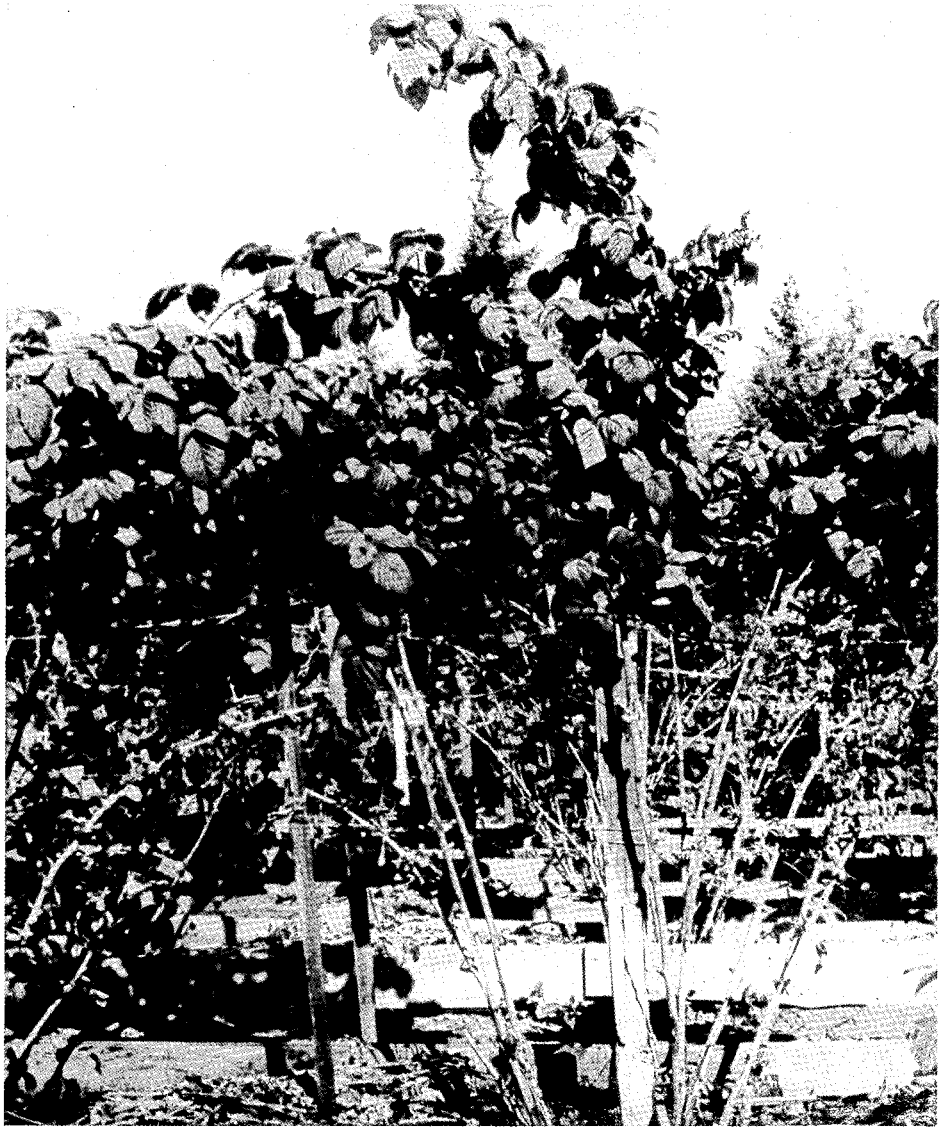
Figure 1 illustrates specimen plants as grown by me in the State of Washington.
Figure 2:
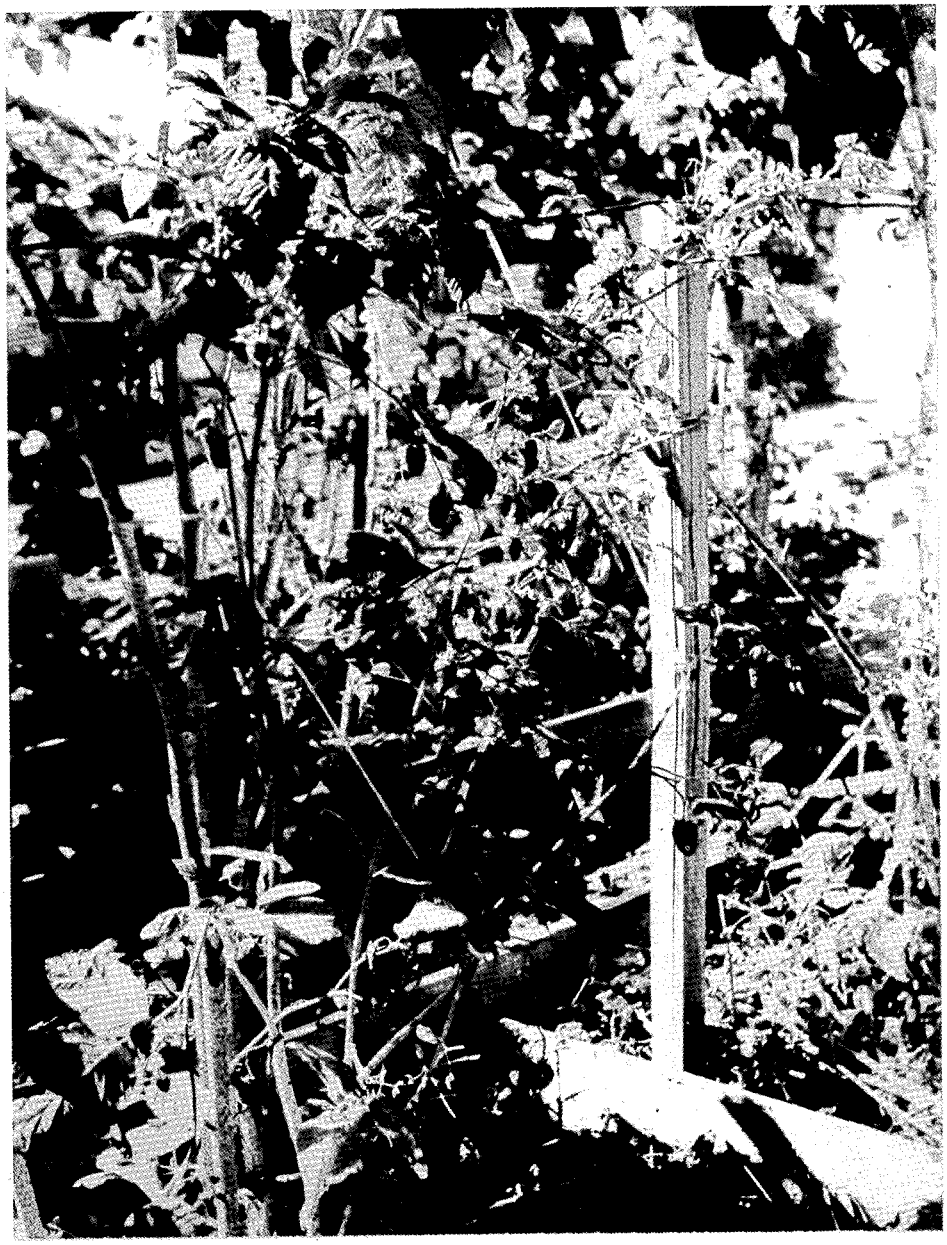
Fig. 2 represents a closer view of said plants grown by me in the State of Washington.

At maturity, the plants obtain a height of about ten feet. In their initial stage they start to grow upright and at about three feet in height they start to incline. They should be supported by props or fences, as are indicated in Figs. 1 and 2 of the drawings, or else the other ends will incline and reach toward the ground.

At maturity the stocks of the plant of my invention average about ¾″ in thickness at the ground and they taper up to a very small tip.

They have very little tendency to side-branch from the spring until fall.

The fruit branches of the plant of my invention will form in spaced relation of about one or two inches on the cane or main stock and they average about 16 inches in length.

The experimental specimens of my invention have shown no tendency toward disease in the plurality of years of their existence. Cane borers have attacked three vines but with little damage as the said vines merely wilted somewhat and in a few days they were normal and healthy again.

The plants of my invention bear fruit about two weeks earlier than raspberries or loganberries reared under similar conditions and bear until late winter. In the peak of the season, plants of my invention have produced twenty-four 16-oz. boxes of berries every two days to six hills of plants.

Figure 3:
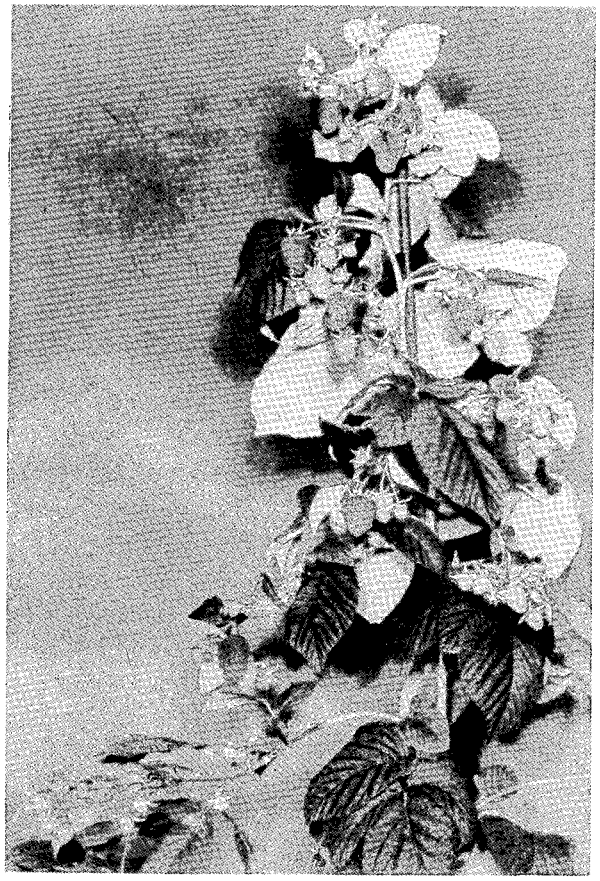
Fig. 3 is a close-up view of leaves and berries of said plant of my invention.

The berries, which are shown in Fig. 3 of the drawings, when mature, compare in size with a mature loganberry, but they pick like a raspberry and leave the core on the vine. In Fig. 2 of the drawings some of the berries are shown and their size is pictorially illustrated. Also, in Fig. 3 of the drawings, berries in various states of maturity are shown and again their size is pictorially illustrated.

The flavor of the berries partakes of both a raspberry and a loganberry and tends to favor the first or the latter depending upon the degree of ripeness. Also, the deepness of their flavor seems to improve as the growing season develops.

When the berries are displayed in their fresh state, they have a particularly appetizing appearance due to their large size, firmness and delicate deep red color. Their flesh is firm and they are competitive with ordinary raspberries in shipping characteristics. The specifications above, and attached drawings, manifest the general characteristics of my new berry, yet it is understood that they may vary in varying climatic and soil conditions.

Character of plant as raised near Port Angeles, Washington:

*Plants—Characteristics*

Size: Cane—generally 9′ to 11′ in height.

Vigor: Very vigorous.

Habit: Upright until about 2′ tall and then inclined to run across the ground, and the plants are trellised throughout their bearing life.

Hardiness: Very hardy.

Productiveness: Exceptionally productive—tendency to produce sequential multiple laterals from same buds and hence prolonged fruiting season.

Susceptibility:

*To insects.*—Average to aphis, attacked by cane borers without destruction of the cane, and no noticeable attack by other insects.

*To diseases.*—Very hardy against diseases and no attack by diseases noticed since the existence of the plants.

Suckers: None.

Canes:

*Diameter.*—Stocky—large diameter, generally on the average of about ¾ of an inch.

*Number.*—Numerous—more than necessary, and pruning is necessary to permit the desired number for a season's growth, such as six from each hill so that three can be trellised in opposite directions.

*Color.*—During the bearing season, the color of the cane varies from the root toward the tip from a deep brown, a brownish red, to a yellowish orange.

*Pubescent.*—No tendency.

*Glabrous.*—Leaves are dark green, exceptionally large, shiny, and neat appearing, and free from hairy appearance.

*Glaucous.*—No overcast.

*Glandular tips.*—None noticeable.

*Eglandular tips.*—Yes.

*Color at tips.*—Yellowish orange.

Prickles: When the canes first start to grow, they are almost identical with loganberry cane and covered with little red stickers. When the cane gets about 16'' to 18'' high, the stickers begin to lose their reddish color. As the cane continues to grow, the cane begins to lose the stickers and during the bearing season, the following year, the cane is practically thornless.

Branches: Very little tendency to side branch.

*Leaves*

Fall: Start to leaf early in the spring and hold their leaves until late in the fall. Compared to Cuthbert Raspberries, they leaf out earlier than said Cuthbert Raspberries and hold their leaves later in the fall than do said Cuthbert Raspberries grown under the same conditions.

Leaflets:

*Number.*—Medium.

*Size.*—Medium—the first leaves are larger than known varieties of raspberries and the second and third leaves follow the same order but are gradually diminishing in size as compared to the first leaves.

Shape: Somewhat rounded and abruptly pointed. Dissimilar to known varieties of raspberries and more like a loganberry leaf.

Width: Wide—widths of 4'' to 5'' for first, full grown leaves are not uncommon.

Length: Long—lengths of 4'' to 5'' for first, full grown leaves are not uncommon.

Thickness: Medium—compared with average loganberry leaves.

Terminal leaflets:

*Base.*—Roundish.

*Shape.*—Generally roundish.

*Apex.*—Abruptly pointed.

Upper surface:

*Color.*—During bearing season, glossy dark green.

*Smooth.*—Smooth in appearance but in contour have medium valleys in ribs.

*Rugose.*—Leaves have ribs and valleys but are not inclined to wrinkle the surfaces of the valleys.

*Pubescent.*—Slightly.

*Glabrous.*—Very slightly hairy and a decided tendency towards smoothness.

Lower surface: Color—greenish white.

Midrib: Slightly prickly.

Margin: Generally dentate and uneven.

Petiole:

*Length.*—Medium.

*Thickness.*—Thick and sturdy.

*Color.*—Brownish red.

*Prickly.*—Very slightly.

*Pubescent.*—Slightly hairy.

*Glabrous.*—Slightly hairy.

*Glandular.*—Not noticeable.

*Eglandular.*—Not noticeable.

*Flowers*

Date of bloom: In the vicinity of Port Angeles, Washington, the plants bloomed approximately two weeks earlier than Cuthbert Raspberries and loganberries grown under the same conditions.

Season of bloom: Early.

Length of blooming season: In the vicinity of Port Angeles, Washington, the blooming season for a plant was substantially two weeks earlier and continued a month and one-half later than Cuthbert Raspberries and loganberries grown under similar conditions.

Color: White.

Number in cluster: Numerous.

Pedicels: The stem supporting the flowers are medium in length, thick and hardy in diameter, slightly prickly and hairy on their surface.

*Prickles.*—Straight but at times slightly curved.

Calyx: In general, the appearance of the blossom was more like that of a loganberry blossom than a Cuthbert Raspberry blossom.

*Fruit—Characteristics*

Season: Bears early and continues to bear very late compared to Cuthbert Raspberries and loganberries grown in the same vicinity.

Borne when: Summer and autumn.

Number of pickings: More pickings than Cuthbert Raspberries and loganberries raised under similar conditions.

Keeping quality: Good.

Shipping quality: Good.

Susceptibility: With normal husbandry, no damage to the fruit has obtained by reason of insects, diseases, drought or sunscald.

Adherence: Cling well.

Picking quality: Very easy.

Size: Large in size and comparable to loganberries grown in the same vicinity. The fruit is substantially uniform in size when ripe and the size tends to increase during the growing season rather than dropping.

Shape: The berry generally simulates in shape a loganberry and has a generally rounded tip portion and enlarged center portion and a base portion which is generally not as large in diameter as the central portion.

Cavity: The cavity is rather deep and rough and compares with the cavity of a raspberry except as to the diameter and length thereof which are both greater.

Bloom: There is a small hair on each lobe of the berry supporting the bloom. Sturdier than either the Lloyd George or the Cuthbert Raspberry—more in comparison to a loganberry.

Drupelets:

*Size.*—Large—very large, comparable to the lobes or drupelets of a loganberry.

*Number.*—Numerous—they are numerous due to the size of the berry and compare favorably with the number found in the loganberry.

Coherence: They have a strong tendency to cling.

Color: Dark red—very similar in color to loganberries grown under the same conditions.

Juice: Juicy.

Texture: Medium.

Flavor: Highly flavored—the berries partake of both a raspberry and a loganberry flavor and tend to favor the first or the latter depending upon the degree of ripeness. Also the deepness of their flavor seems to improve as the growing season develops.

Quality: Best.

Use: Dessert, kitchen, market, home, freezing, and canning.

*Desirability*

The plant is desirable because of the large size of the berries, their distinctive flavor which partakes of some of the aspects of a raspberry and some of the aspects of a loganberry, and their long bearing season. Also the plants are desirable because of the fact that the berries ship well, keep well, pick well, and may be used in various ways, including use of the fresh fruit, use for jams and jellies, use in canning and use for frozen storage. The berries are relatively high in pectin content which makes them well suited for making jam or jelly therefrom. Also, their seeds are less objectionable than those of raspberries, particularly when eaten fresh.

*Origin*

During one spring, I heeled in a number of berry plants of four varieties, e. g. boysenberry, loganberry, Cuthbert Raspberry and St. Regis Everbearing Raspberries. These plants were left heeled in until the following late spring. Most of the plants died but those that were alive, of each variety, were set out. At the base of one of the loganberry plants, a sport appeared during the summer of that year. This sport did not have the appearance of any of the berry plants which I had heeled in. While I did not remove all of the dirt to positively determine whether the sport had appeared from the tissues of the loganberry, it gave the appearance of so doing. Expert advice given to me is that the sport probably appeared from the tissues from either one of the Cuthbert Raspberry plants or one of the St. Regis Everbearing Raspberry plants. After finding this sport, careful and practical nursery attention was given this sport to cause it to mature. After maturity of the sport, other plants were reproduced from the sport and experimental plants were propagated to determine whether or not the plant could be caused to repropagate itself to kind in nature. After growing a great number of these plants, it was found that they did not tend to revert back to one particular stock of those from which it apparently grew.

The plant varieties referred to herein by the names of loganberry, Cuthbert Raspberry, Lloyd George, boysenberry, and St. Regis Everbearing, are not patented varieties.

*Parentage*

Probably a sport from a raspberry plant.

*Source of stock*

Not certain, as I obtained plants from many sources, and started many plants from tip sets.

I claim:

The new and distinct variety of plant of the red raspberry type, as described and illustrated, characterized as to novelty by the canes of the plant having no tendency to sucker and a tendency to produce sequential multiple laterals from the same buds resulting in a prolonged fruiting season, by having canes which grow upright for a short distance and then bend over to a horizontal position and are easily trained over horizontal trellises, by having large berries of a size and shape simulating loganberries grown under similar conditions, and by having berries which pick like raspberries.

FRANK A. NEWBERRY.

REFERENCES CITED

The following references are of record in the file of this patent:

UNITED STATES PATENTS

| Number | Name | Date |
|---|---|---|
| Pl. Pt. 779 | Toms | Jan. 13, 1948 |